United States Patent
Drinan et al.

(10) Patent No.: US 6,354,996 B1
(45) Date of Patent: Mar. 12, 2002

(54) BODY COMPOSITION ANALYZER WITH TREND DISPLAY

(75) Inventors: Darrel Drinan, San Diego; Jeffrey I. Levatter, Rancho Santa Fe, both of CA (US); Diethard Merz, Darmstadt (DE); Adrian P. Alting-Mees, Vista, CA (US)

(73) Assignee: Braun GmbH, Kronberg (DE)

(*) Notice: Subject to any disclaimer, the term of this patent is extended or adjusted under 35 U.S.C. 154(b) by 0 days.

(21) Appl. No.: 09/291,546

(22) Filed: Apr. 14, 1999

Related U.S. Application Data

(60) Provisional application No. 60/081,886, filed on Apr. 15, 1998.

(51) Int. Cl.[7] .................................................. A61B 5/00
(52) U.S. Cl. .......................... 600/300; 600/301; 128/903
(58) Field of Search .............................. 600/300–301, 600/547; 128/903, 900, 920–925; 705/2, 3; 379/106.02

(56) References Cited

U.S. PATENT DOCUMENTS

| | | |
|---|---|---|
| 4,301,879 A | 11/1981 | Dubow |
| 4,694,922 A | 9/1987 | Mairot |
| 5,372,141 A | 12/1994 | Gallup et al. |
| 5,410,471 A * | 4/1995 | Alyfuku et al. ............. 600/300 |
| 5,415,176 A | 5/1995 | Sato et al. |
| 5,697,376 A * | 12/1997 | Nomura et al ............... 600/300 |
| 5,704,350 A * | 1/1998 | Williams, III ............... 600/300 |
| 5,817,031 A * | 10/1998 | Masuo et al. ................ 600/547 |
| 5,974,124 A * | 10/1999 | Schlueter, Jr. et al. ....... 600/300 |

FOREIGN PATENT DOCUMENTS

WO   WO9608198 A1   3/1996

* cited by examiner

Primary Examiner—John P. Lacyk
Assistant Examiner—Michael Astorino
(74) Attorney, Agent, or Firm—Hopgood, Calimafde, Judlowe & Mondolino LLP

(57) ABSTRACT

A body composition analysis and display system provides a display of averaged data for selected body composition factors, such as body weight and body fat percentage, at a plurality of selected intervals over a period of time. The user's body fat percentage is determined by measuring the user's body impedance.

63 Claims, 12 Drawing Sheets

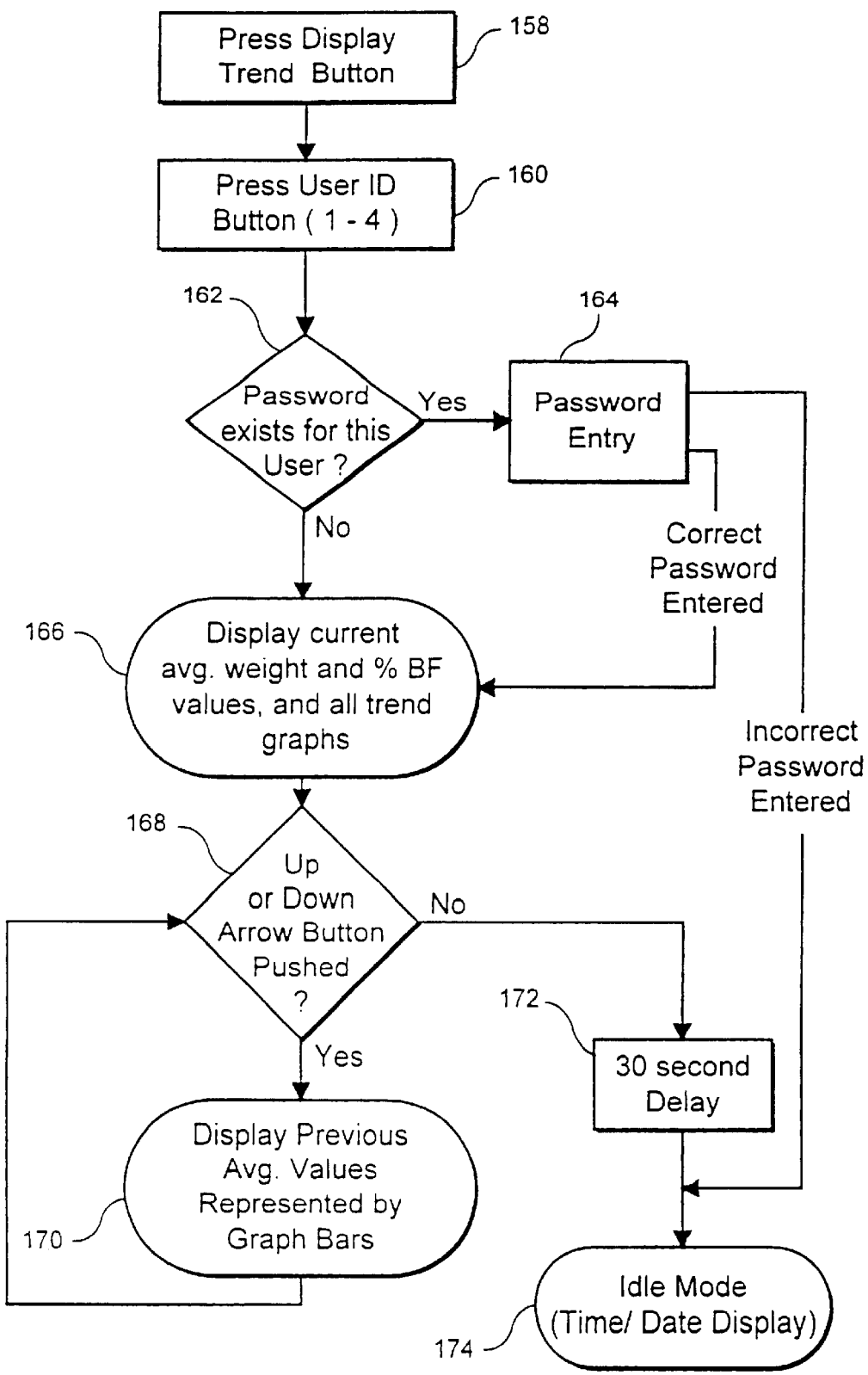
F I G. 10

BODY COMPOSITION ANALYZER WITH TREND DISPLAY

RELATED APPLICATIONS

This application is based on a provisional application Ser. No. 60/081,886 filed on Apr. 15, 1998, the contents of which are incorporated herein by reference.

FIELD OF THE INVENTION

The present invention relates generally to the measurement of body composition, and more particularly to a bioelectrical body composition analyzer that displays trend data of one or more body composition factors, such as weight and body fat.

BACKGROUND OF THE INVENTION

In recent years, there has been an increasing interest among health-conscious individuals to monitor, on a continuing basis, certain of their physical parameters, or attributes, such as their body weight, blood pressure and heart rate. There has also been an increasing interest, particularly among dieters and individuals who engage in exercise or athletic activities, to obtain an accurate determination of the percentage of their weight that is made up of body fat.

It has long been known that the risk of developing certain life-shortening illnesses, such as coronary artery disease, hypertension and diabetes, is related to obesity. It has recently been determined that the health risks associated with obesity are more related to increased body fat than to increased body weight per se. Too little body fat also poses a health risk because the body requires a certain amount of fat for certain normal physiological functions such as cell membrane formation and thermal insulation.

A number of methods are known to determine the body composition in vivo. The most accurate of these are, however, expensive and time-consuming methods such as dual x-ray absorptiometry, dilution techniques and computer topography. These methods, because of their expense and complexity, are not suitable for use in the home or as a consumer device. Other less costly and complex procedures for measuring body fat content are also known.

One such technique, near infrared interaction, is based on the observation that human body fat absorbs light in the near-infrared spectrum. The percent of body fat is calculated from the value of absorbed infrared light in combination with the individual's height and weight. The main drawback of this technique is that the measurement is made at only one location of the body; its accuracy has also been questioned.

In another known technique to determine body fat content, the thickness of skinfolds formed at defined body sites is measured. The sum of these thicknesses correlates with body fat content. Although this method is one of the most commonly used methods to determine body fat, its use requires a considerable level of skill and training in order to obtain reproducible results. Moreover, since several sites of measurement are very difficult to reach this technique is impractical for use by the person who is trying to make a measurement of his or her body fat.

The use of ultrasound to measure the thickness of the fat layer of the skin, another known technique to measure body fat, involves the reflection of ultrasound waves at the boundaries of the skin layers; the delay of reflected pulses is proportional to that layer of thickness. The major drawbacks in this technique are the need to use fluid for introducing the ultrasound into the skin, the variability of the thickness as a function of pressure and the often observed inaccuracy due to artifacts and reflections at components other than the skin boundaries.

It is known that body fat content as a percentage of total body weight may be measured by measuring the body's electrical impedance, such as between the individuals feet or between the foot and arm. This technique is known as a bioelectric impedance analysis (BIA). As disclosed in U.S. Pat. No. 5,415,176, body impedance along with the individual's height and weight can be used to calculate an estimate of the individual's body density and body fat percentage by the use of a known algorithm that relates body fat to body impedance.

The use of bioelectric impedance analysis to measure body composition, and specifically body fat, is based on the different conductive and dielectric properties of various biological tissues at various frequencies of current. Tissues that contain a lot of water and electrolytes are highly conductive, whereas fat, bone, and air-filled spaces such as the lungs are highly resistive or dielectric tissues. The volume of these tissues can thus be determined from measurements of their combined resistances.

As shown in U.S. Pat. No. 5,415,176, in a typical BIA measurement a pair of electrodes is applied to the individual's extremities such as the hands or feet. Low-current (less than 1mA) source or generator is applied across a first pair of electrodes, and the voltage across a second pair of electrodes is measured. Since the value of current is known, the voltage drop provides an accurate indication of the body's impedance. The body impedance, determined in this manner, along with the individual's body weight and height, can then, as noted, be used to calculate or estimate the individual's body fat or body density.

Although the knowledge of an individual's body fat is of considerable value, more useful information in this regard would be an indication of body composition, such as body fat, over time, such as over a period of weeks or months. Such historical information is particularly valuable to individuals who are on a diet or fitness program as an indication of the progress they have made in reducing body fat or weight over a period of time. This trend information allows the individual to better monitor and thus control his or her progress in reducing body fat and body weight by being able to observe the change over time of weight and/or body fat percentage.

A system that provides such a so-called historical or trend display of body weight over a specified period of time is disclosed, for example, in U.S. Pat. Nos. 3,512,592 and 4,301,879. As shown in the latter, weight data from prior measurements are stored in memory and extracted, along with time data, to generate a display that represents the individual's body weight as a function of time.

The prior body weight trend display systems are, however, complicated to use and provide only limited information with regard to the displayed variations of body weight. Particularly, the known systems are typically usable by only one individual and only provide information on a single aspect of body composition namely body weight. Moreover, the known body measurement and display systems are often not accurate, and the measured data is often not repeatable, because, for example, they fail to take into account variations in body fluid content that occur during the day, and they do not provide averaging of multiple body measurements.

SUMMARY OF THE INVENTION

The body composition analyzer of the present invention provides a display of the user's current body composition parameters such as body fat content or percentage and/or body weight, as well as a display of the prior trend or historical data of those parameters over a period of time. The analyzer base unit, in one embodiment of the invention, includes a set of electrodes connected to a current source to provide an electrical signal representative of the user's bioelectrical impedance or bioimpedance, which is used to compute the user's body fat percentage. This information and the user's measured body weight may be displayed on the base unit and/or transmitted to a remote display unit.

In one embodiment of the invention herein disclosed, the user places the front part of his or her foot on a pair of sensor electrodes and heels on a pair of stimulus electrodes. The measured voltage drop across the sense electrodes is proportional to the impedance (resistance) between the sense and stimulus electrodes, and is indicative of the user's body fat percentage. A load cell in the base unit produces an additional signal that represent the user's body weight. The body weight and body fat (impedance) measurement sequence is controlled by a microprocessor that also computes the user's body fat percentage in accordance with an algorithm stored in its software as a function of the measured bioimpedance along with other factors, such as the user's height and weight.

The user's current body fat percentage and body weight data are displayed as a numerical readout, along with graphical trend data of those parameters based on a series of prior measurements of body fat percentage and body weight taken at specified (e.g. weekly or monthly) intervals. Each time a new measurement of body weight and body fat percentage is made, the current data is displayed along with the stored results of prior measurements of those parameters to provide a trend or historical data for the user that indicates how these body composition factors have changed over time.

In a further aspect of the invention, the displayed trend data (e.g. body weight and body fat percentage) are average values of measurements taken during each display interval. Thus, if trend data is displayed for each week, and the user has made two or more measurements in any single week, the values of those measured body weight and body fat percentage measurements are averaged, and the computed average body weight and body fat percentage data are stored in memory for later display.

In a further aspect of the invention, a number of different authorized users may employ the body composition analyzer to display their current and body composition trend data. To this end, an authorized user, before making a new measurement, enters his or her unique identification code so that only previously stored measured body composition data for that user is taken from the memory to create a trend display for that user. Information concerning each authorized user's height, gender and the like is also stored in memory to allow a computation of, e.g., body fat percentage, to be made for that user.

In yet a further aspect of the invention, measurements of body composition factors taken during certain times of the day outside of a prescribed time interval or window (e.g. in the morning), are displayed, but not stored for inclusion in trend history with other body composition measurements taken during the prescribed time interval. In this manner, the body composition trend data that is displayed is more accurate since it reflects measurements made during the same time of day over a period of weeks or months, and, as a result, is not affected by the normal variations of body fluid content and weight that occur in most individuals during the course of a day.

In a further aspect of the present invention, use of and access to the system by an unauthorized user is prevented by comparing a current body composition measurement for a user who has entered one of the available personal identification codes against stored prior body composition data for the user to whom that identification code has been assigned. If the current measurement deviates from the stored data by a predetermined amount for a given time period, e.g. 5 percent for a one-week interval, the user is identified as being unauthorized and is prevented from gaining access to any of the stored data.

The present invention relates to a body composition trend data analyzer and display system, substantially as defined in the appended claims and as described in the following detailed specification as considered together with the accompanying drawings, in which:

BRIEF DESCRIPTION OF THE DRAWINGS

FIGS. 7, 8, 9, and 10 are logic flow diagrams describing different sequences of operation of the body composition analyzer of the invention.

DETAILED DESCRIPTION OF THE PREFERRED EMBODIMENT

Figure 1A:
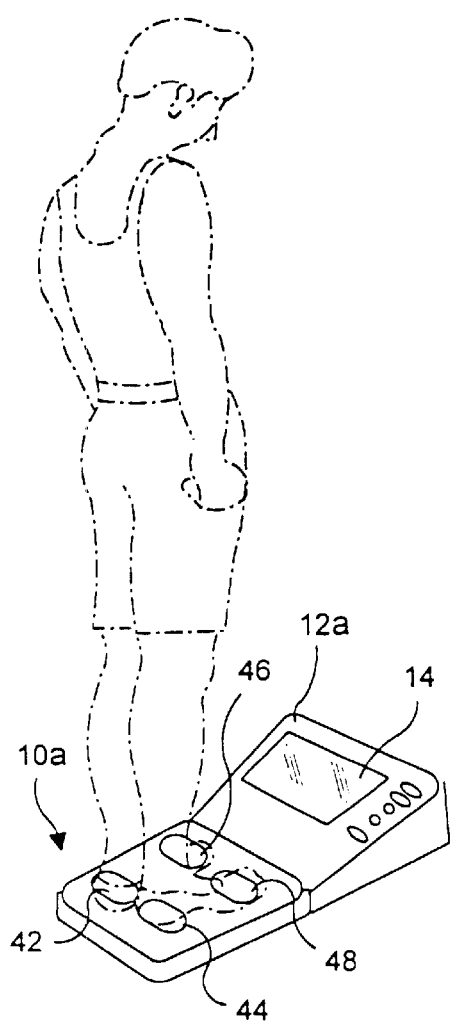
FIGS. 1A and B are isometric views showing the use of the body composition analyzer in accordance with two embodiments of the invention.
Figure 1B:
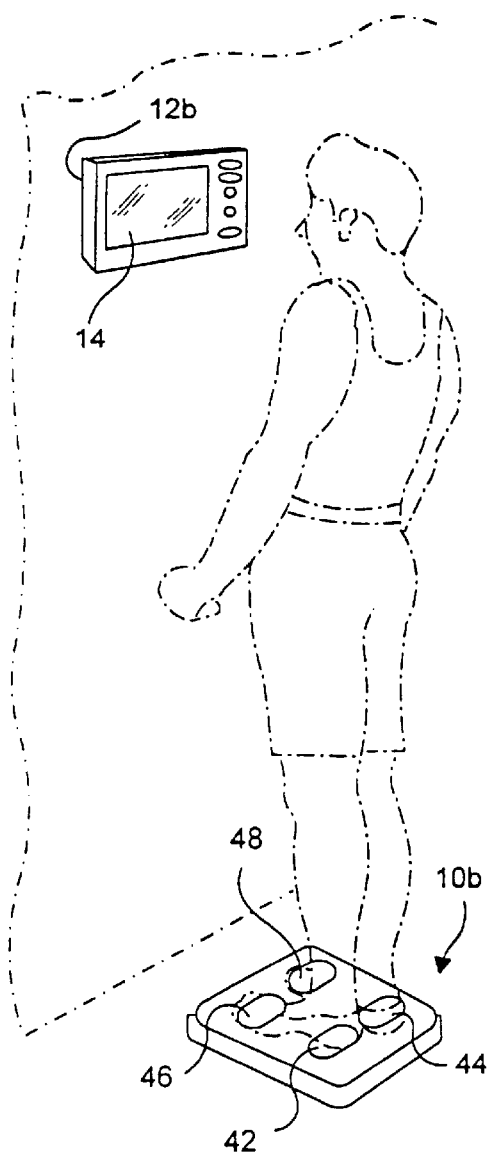
Figure 4A:
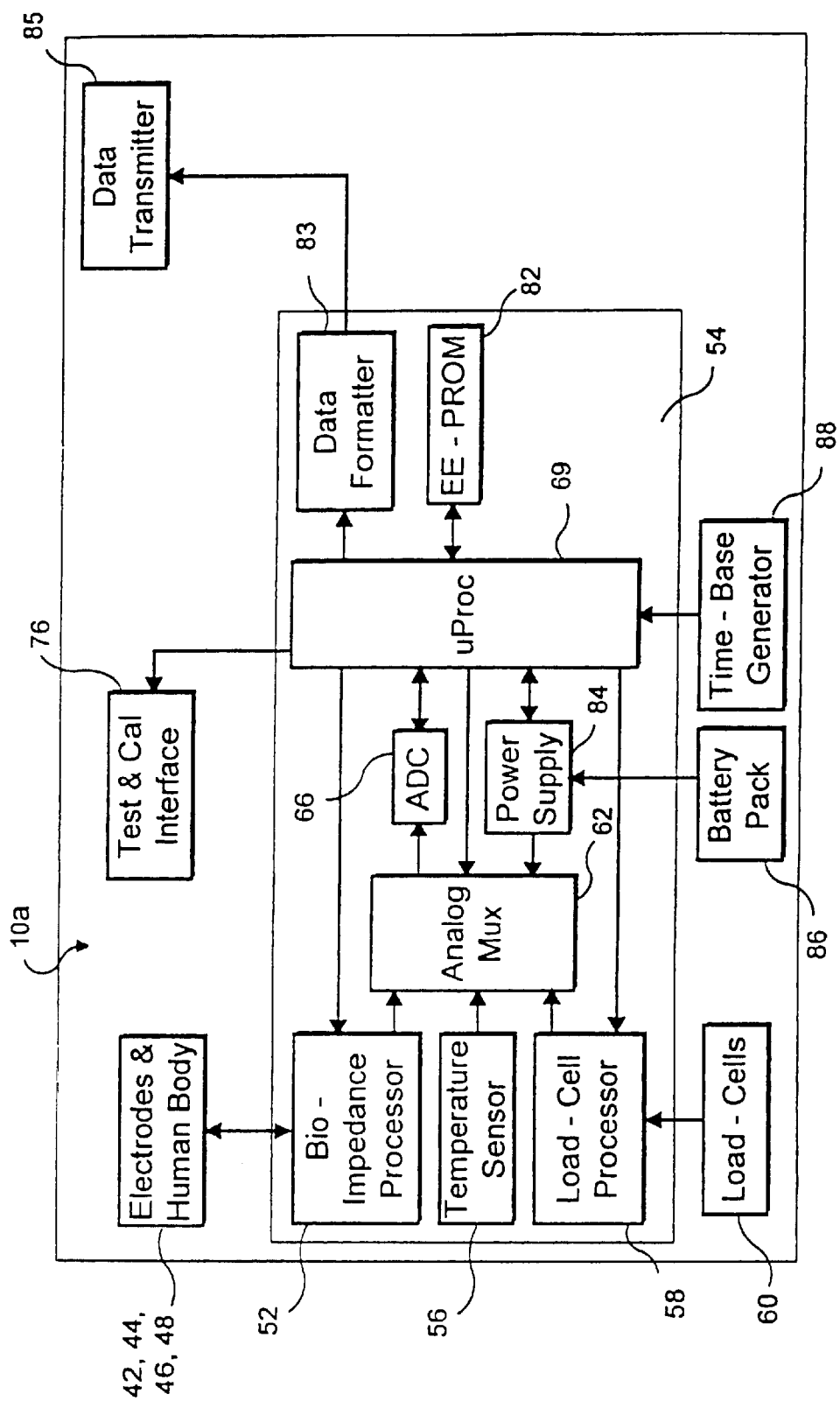
FIGS. 4A and 4B are schematic block diagrams of a body composition analyzer in which the display unit is remote from the base unit in accordance with a second embodiment of the invention.
Figure 4B:
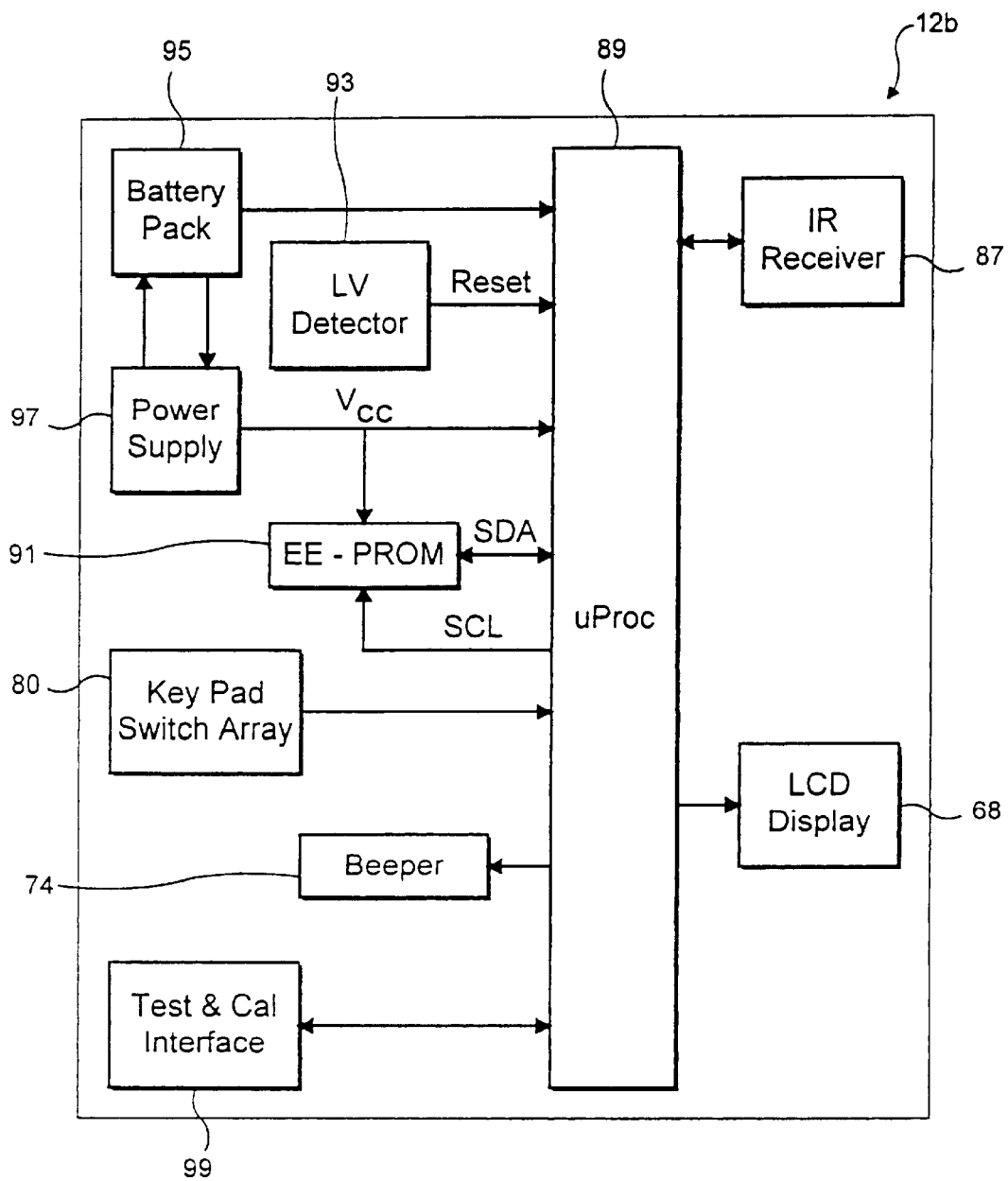
Figure 5:
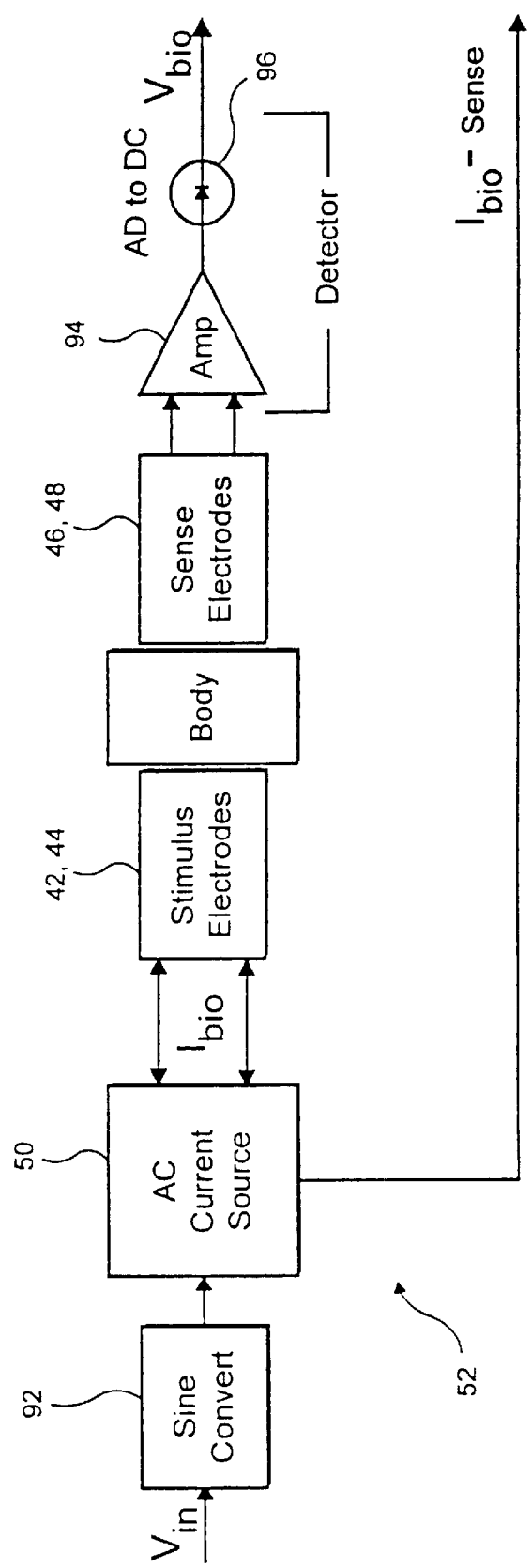
FIG. 5 is a schematic diagram of a bioimpedance processor that may be used in the base unit of the body composition analyzers of FIGS. 3 and 4A.

The body composition analyzer system of the invention, as in the embodiments generally designated as 10a and 10b in FIG. 5, 1A and 1B respectively, measures, computes and displays certain body composition attributes, such as body fat percentage and body weight. It will be understood that the system of the invention may also be used to measure and display other body attributes such as fat-free mass, lean body mass, body mass index, total body water, blood pressure, and other parameters which affect the body's bioimpedance. The body composition analyzer of the invention may be incorporated in a unitary base assembly 10a, as in the embodiment of FIG. 1A, and includes a graphic display unit 12a, which displays the current measured and computed body composition information along with a trend display of corresponding information obtained in prior measurements taken during a selected number of prior time intervals (e.g. a week). The measured body composition information, both current and trend data, may also be displayed at a remote display unit 12b, separate from the base unit 10b, as described in greater detail below with reference to the embodiment of the invention illustrated in FIGS. 4A and 4B.

The graphical body composition trend information is, according to one aspect of the invention, produced of the average computed values of specified body composition attributes that were measured during a selected display interval. If desired, maximum or minimum values of body composition attributes that are measured during that interval, or any other value of a body composition attribute that may be of interest, may also be computed and displayed. Thus, if weekly trend information is displayed, and a body composition measurement is made more than once during any given week, the displayed information for that week (or maximum or minimum) is computed as the average of the two or more measurements made during that week.

Figure 2:
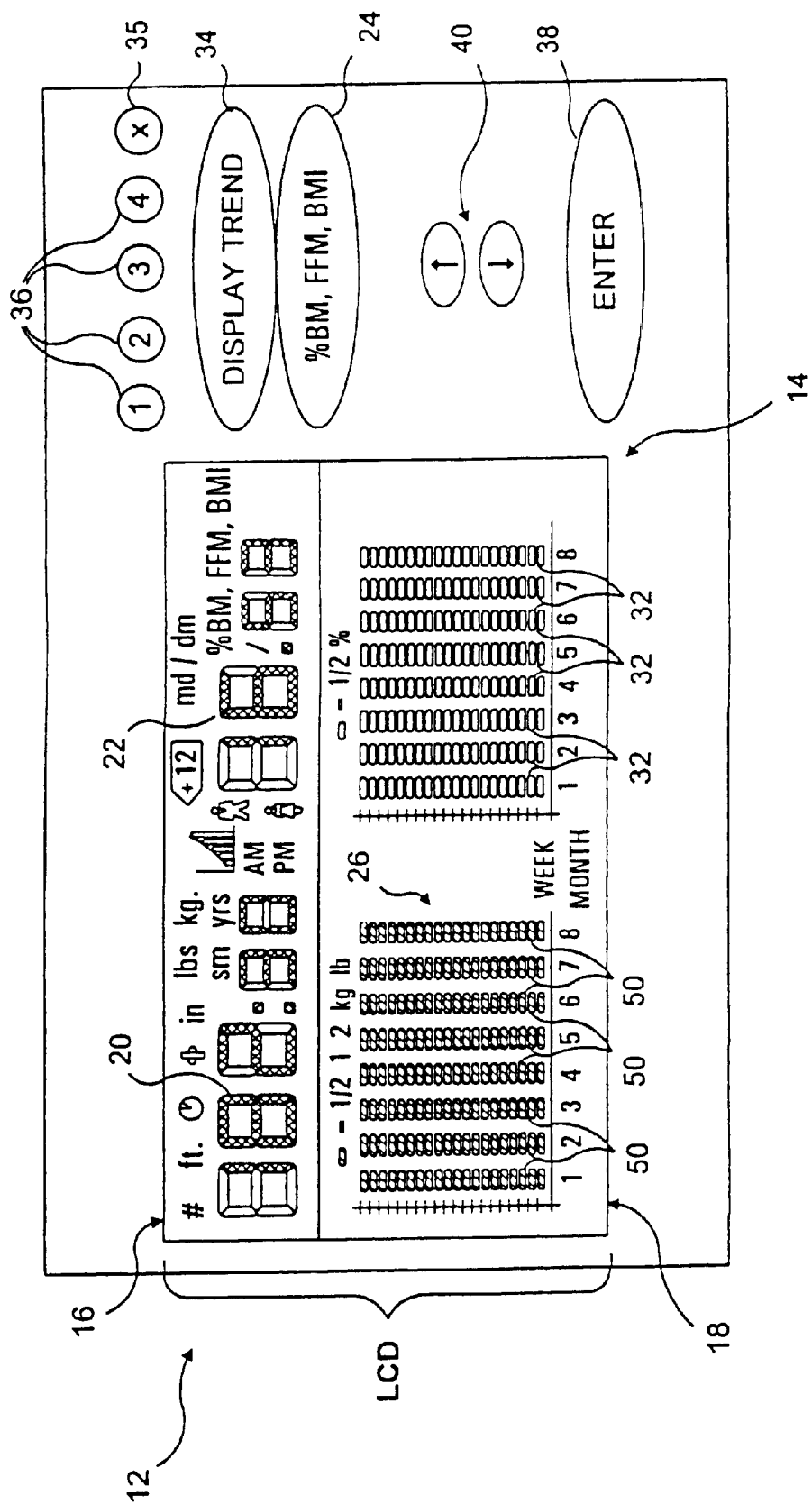
FIG. 2 an elevation of a display unit that provides a display of body fat percentage and body weight as used in the body composition analyzer of the invention.

As shown in FIG. 2, the graphic display unit 12, which, as noted, may be formed integral with the sensor unit or separate and remote therefrom, includes a viewing section 14 that has a numerical value area 16 and a trend graph area 18, which respectively provide an LED numerical display and graphical displays. Area 16 provides a first numerical indication of the user's body weight at 20, and a second numerical indication of either the user's body fat percentage, fat free mass, or body mass index in accordance with the user's choice made by operation of the display button 24. The fat free mass is the inverse of the body fat percentage, and the body mass index is the ratio of the square of the user's height to his or her weight.

The trend graph area 18 includes a first bar graph display 26 that includes a plurality (here eight) of vertical bars 30. The height of each bar 30 is proportional to the average value of body weight for each time interval (week) for an eight-week period, as indicated by the numerals 1–8. Similarly, a second plurality of bars 32 indicate the trend over a similar eight-week period, for example, of the user's body fat percentage. For each series of bar graphs 30, 32, bar 8 represents the current or last-taken body fat or body weight measurement. To provide a clear visual display of the trend data, the bars 30 indicating body weight and bar 32 indicating body fat percentage may be of contrasting colors, as indicated in FIG. 2. The bars 30, 32 may also be of contrasting shapes or patterns, or they may be positioned at different locations of the trend graph display. The body weight and body fat percentage trends are displayed upon the operation of the display trend button 34.

The body composition analyzer of the invention may display trend body composition data for a plurality, here four, different authorized users. To this end, each authorized user is assigned a code number, here shown as 1, 2, 3 or 4. At the beginning of each measurement the user inputs his/her personal code input at the corresponding numbered select button 36, so that the trend display produced in display area 18 will be unique for that user. The use of the analyzer by a guest user, as described in greater detail below, is enabled by the operation of the guest (x) button 35. The operation of the enter button 38 selects the currently displayed option and the operation of the up/down arrows button 40 allows the user to scroll through the options displayed in areas 16, 18.

Figure 6:
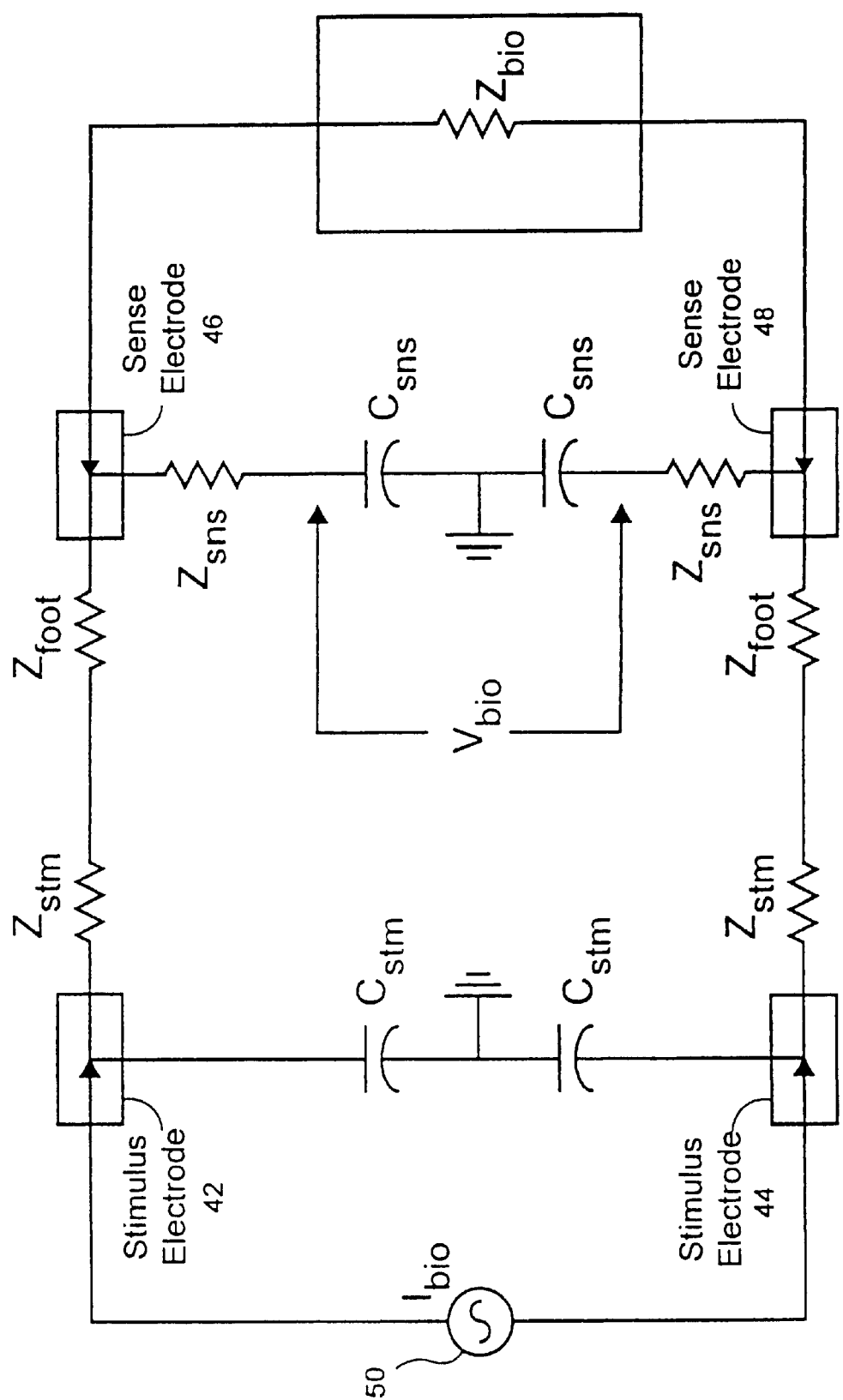
FIG. 6 is a schematic circuit diagram of the stimulus and sense electrodes of the bioimpedance processor of FIG. 5.

The base unit of the body composition analyzer, which may have the general overall appearance and size of a conventional bathroom scale, includes, as in the embodiments of the invention illustrated in FIGS. 1A and 1B, a pair of heel or sense electrodes 42, 44, and a pair of toe or stimulus electrodes 46, 48 on its upper surface. The base unit also includes, as shown in FIGS. 5 and 6, a bioimpedance processor 52 that includes a constant current generator 50 connected to stimulus electrodes 46, 48. Current generator 50 supplies an imperceptibly low-level alternating current at a typical frequency of 50 kHz to electrodes 42, 44. As described in greater detail below, the bioimpedance processor 52 senses a voltage $V_{Bio}$ across the sense electrodes, 42, 44 which, along with the sensed current $I_{Bio}$, is used to compute the user's bioimpedance $Z_{Bio}$, which, in turn, is used to compute the user's body fat percentage.

The control or sensor unit 54 included in the base unit also includes a temperature sensor 56 and a load cell processor 58 which receive an analog voltage from an external load cell 60 that is proportional to the user's body weight. Load cell 60 may include a plurality of resistances that vary in accordance with the user's weight and which are configured as a Wheatstone bridge to produce an analog voltage that is proportional to the value of that resistance.

The analog output voltage of the bioimpedance processor 52, temperature sensor 56 and load cell processor 58, which respectively indicate the user's bioimpedance, the ambient temperature, and the user's weight, are applied to the inputs of an analog multiplexer 62, which also receives a control signal from a microprocessor 64. The ambient temperature is sensed and measured in the microprocessor to make adjustments for thermal drifts. The output of the multiplexer 62 is applied to the input of an analog-to-digital converter (ADC) 66 which converts the selected output analog signal of the multiplexer 62 to a corresponding digital signal, which, in turn, is applied to an input of the microprocessor 64.

The microprocessor 64 also receives the user's identification and previously entered data regarding the user's height, sex, and fitness level. Microprocessor 64 contains appropriate software to perform specified control and computation functions including the computation of the user's body fat percentage from the input bioimpedance and the other input data in accordance with an algorithm, such as the following:

$X = a*ht^2/Z + b*wt + c*age + d*sex + e*FL + f$ where a, b, c, d, e, and f are constants ht=height Z=body bioimpedance wt=weight sex=%for male/female FL=fitness level X=body fat percentage The weight and body fat percentage data computed in microprocessor 64 is applied to an LCD display 68 to provide a visible numerical display of that data, as illustrated in FIG. 2. The output of microprocessor 64 may also, as shown, be applied to an LED drive 70 the output of which is applied to LED indicators 72, which provide visual information to the user of system status, e.g., when a measurement sequence has been completed, and the detection of an error condition. Status information in audible form may also be provided by a beeper 74 which receives status information from the microprocessor 64. An output of microprocessor 64 may also be applied to a test and calibration interface 76, which includes a set of electrical contacts that allows serial data to be transferred between the microprocessor and a remote test and calibration station (not shown).

A key matrix 80 included in the sensor unit 54 is employed by the individual to enter data to the microprocessor 64 such as his/her personal identification number, height, gender, age, and physical profile, the latter being represented in an increasing order of fitness by a number from 1 to 5. An output of the microprocessor 64 is also connected to receive data from, and transmit data to a data memory, here shown as an EEPROM 82.

Also included in the base control unit 54 is a power supply 84 which supplies a d.c. operating voltage to the multiplexer 62 and microprocessor 64. Power supply 84 receives its operating voltage from an external battery pack 86. An external time base or system clock generator 88 provides clock signals at a predetermined frequency to the microprocessor 64 to control the computation and general digital processing functions that are performed in the microprocessor.

Referring again to FIG. 5, the bioimpedance processor further includes a sine converter circuit 92 which receives a logic control signal Vin from the microprocessor 64 and converts that signal to a sinusoidal signal with a minimally low harmonic content. The sinusoidal output voltage of circuit 92 is converted in current source 50 to a programmed control current Ibio that is applied, as described above, to the stimulus electrodes 46, 48. The a.c. output of the sense electrodes 42, 44 is applied to a detector that includes an amplifier 94 and a rectifier 96 that converts the ac output of the sense electrodes to a voltage $V_{bio}$. The ratio of voltage $V_{bio}$ and the current $I_{Blo}$ is the bioimpedance $Z_{bio}$, which is processed in the microprocessor 64, as described above, to compute the body fat percentage.

In the embodiment of the invention illustrated in FIGS. 1B, 4A and 4B, the body composition analyzer of the invention is divided into two components, a base sensor unit 10b schematically illustrated in FIG. 4A and a remote display unit 12b schematically illustrated in FIG. 4B. The display unit 12b may, for example, be mounted on the wall at the eye level of the user to permit the user to more conveniently view the graphic display of his/her body composition information.

Figure 3:
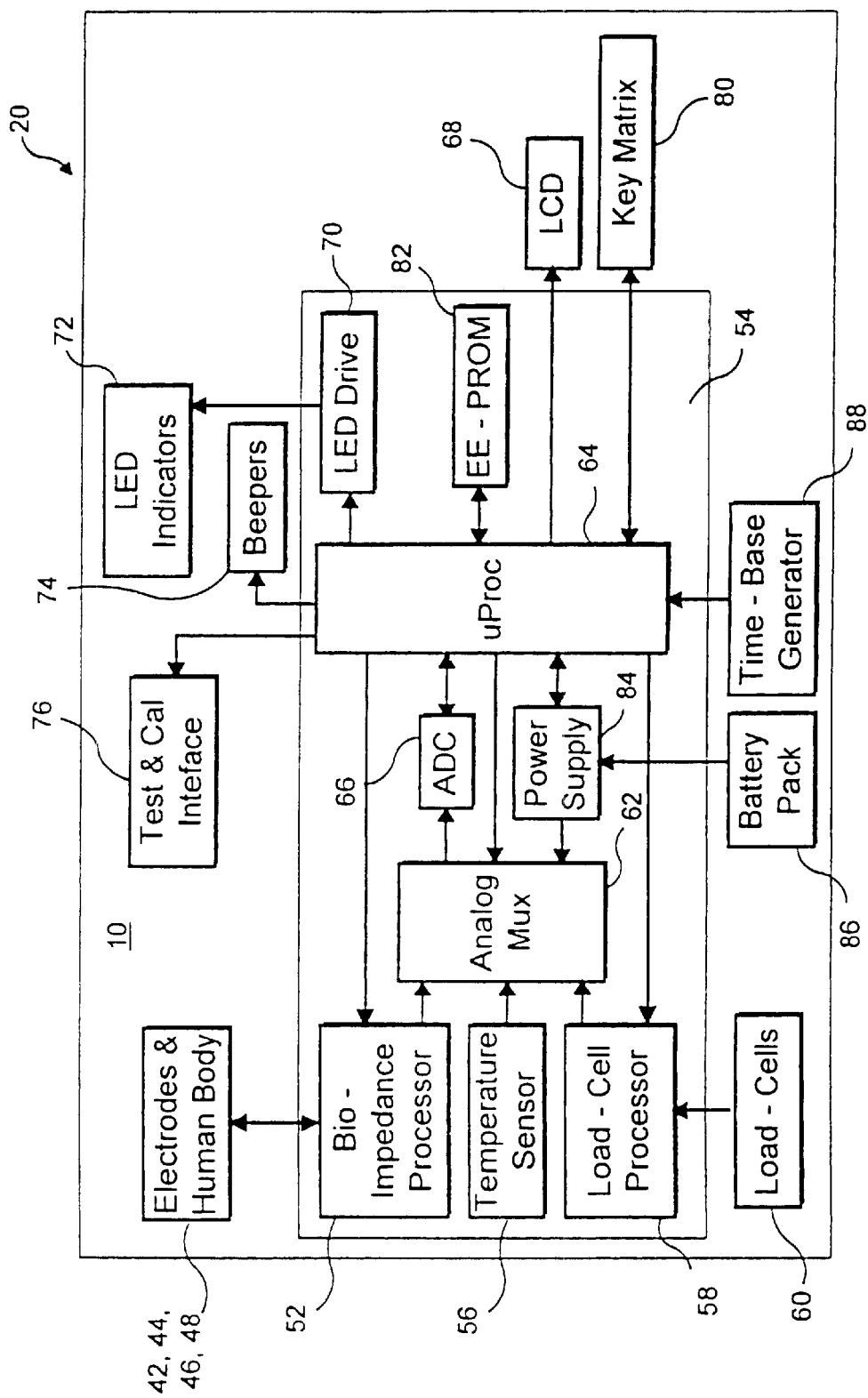
FIG. 3 is a schematic functional block diagram of the body composition analyzer in accordance with a first embodiment of the invention.

The sensor unit 10b of FIG. 4A contains many of the components included in the body composition analyzer unit of FIG. 3, and are identified by corresponding reference numerals to those employed in FIG. 3. However, the graphical display 68 and key matrix components are, in the embodiment of FIGS. 4A and 4B, included in the remote display unit 12b, rather than in the sensor unit. Also included in display unit 12b, rather than in the sensor unit, is the beeper 74.

To allow the measured body composition information measured and computed in the sensor unit 10b to be displayed in the remote graphic display unit 12b, the sensor unit further includes a data formatter 83, which receives the computed weight and body fat percentage information from the output of microprocessor 64. Data formatter 83 which modulates a carrier signal with the binary coded data first received from the microprocessor.

The data sensor unit 10b also includes a data formatter 83, which electrically alters the form of the coded data to achieve increased efficiency of data transmission through a data transmitter 85, which receives the encoded body composition data from data formatter 83. Data transmitter 85, which transmits the current and average body composition data to the remote display unit 12b, preferably includes one or a plurality of infra-red (IR) light-emitting diodes (LEDs) that convert the data to light. The encoded body composition data transmitted from data transmitter 85 is received at the remote display unit 11 by an IR receiver 87. The latter is coupled to a display microprocessor 89, which processes that data and produces information signals to an LCD display 68, which is similar to the one described above with reference to FIGS. 2 and 3.

The remote display unit 12b includes, as shown in FIG. 4B, its own memory, here shown in the form of an EEPROM 91, that is connected to the inputs of microprocessor 89 to store previously computed trend body composition data and the relevant user data that was entered in the key pad matrix switch array 80, which, in the embodiment of FIG. 4B, is included in the display unit 12b. The trend data and user data are transmitted between the EEPROM 91 and microprocessor 84 via the SCL and SDA lines.

The remote display unit 12b includes its own battery pack 95 and power supply 97 to supply the operating voltages to the microprocessor 89 and memory 91, as well as its own test and calibrate interface 99. An LV detector 93 in the display unit 11 detects the occurrence of a low battery voltage level, and applies a signal to microprocessor 89 when that occurs to provide an indication at LCD display 68 of a low-voltage condition. LV detector 93 sends a reset signal to the microprocessor 85 when the batteries are removed or replaced in battery pack 95, or when the battery voltage drops further below the low battery limit that turns on the LCD indicator.

The operation of the body composition analyzer of FIGS. 4A and 4B is similar to that of FIG. 3 except that the user's information data is input by the use the keyboard matrix located in the remote display unit, and the current and averaged body composition information is displayed graphically at the remote visual display unit. The user, as in the previously described embodiment of FIG. 3, and as shown in FIG. 1B, stands on the heel and toe electrodes 42, 44, 46 and 48 provided in the sensor unit 10b to provide the data which are processed by the microprocessor to compute the user's body weight and bioimpedance using the data from the sensor unit. From this data, the display unit microprocessor 89 computes the user's body fat percentage as described previously.

As described above, in addition to the user's current weight and body fat percentage data, historical or trend data of these body composition factors may also be displayed on the display unit. This trend data is computed from body weight and body fat percentage measurements that were taken previously at different times over selected time periods, such as during eight consecutive weeks, or eight months. As shown in FIG. 2, the trend data may be displayed in a plurality of columns 30, 32 each of which represents either an entire week or an entire month of the user's averaged weight or body fat percentage. To this end, data of the current body weight and body fat percentage measurements and a plurality of prior body fat percentage and body weight measurements for up to four different users is stored in memory 84. When any authorized user operates the test display button 34, that stored prior body measurement data is taken from memory and inputted to the microprocessor 64. It is then displayed along with the authorized user's current body weight and body fat percentage on bar graphs 30, 32.

At the onset of a typical use of the body composition analyzer of the invention, the weight and body fat percentage trend data for that user is displayed in a single bar, which represents the user's average weight/body fat percentage for the first week. After the first week, a second bar appears, which represents the user's average weight/body fat percentage for the second week of measurements. Each day during the second week in which a measurement is taken, that day's values are averaged into the totals for that week. This weekly trend continues until, say, the ninth week, at which time the eight-week trend graph is collapsed back into two bars. At this point, the data for the first four weeks are averaged and converted into a bar for the first month, and the data for the second four weeks of data are averaged and converted into the second month bar. Successive measurements are then averaged into the current month and additional month bars will appear as time continues.

At the end of eight months, the data for the first month are deleted and the data displays of all the subsequent months shift down one position in the 1–8 bar graph (i.e. previous month 2 is now shown in bar #1 position, and previous month 3 is now shown in bar #2). In this way, the user always has an eight-month window in which to graphically view his/her weight and body fat percentage trends. It is to be noted that a missing measurement during one specified interval that may affect the respective interval e.g. week, is cancelled within the trend display so that missing measurements do not adversely affect the overall trend function.

As noted, the trend body fat percentage and body weight information stored and displayed in the system of the invention are averages for measurements made during a preselected period, such as one week, the same period as the intervals between the bar graph displays 30, 32. Thus, for example, if a user makes three measurements of his/her body weight and body fat percentage during week 1, the graphical data for that week on the display unit will be the average of those three measurements of these measured body components.

To this end, body weight and body fat percentage data, which was measured and computed during a given week, in the manner described above, are stored in memory 82. If an additional measurement is performed during that same week, the previously stored values of body weight and body fat percentage for that week are recalled from memory 84, and an average of the previous and current measurements is calculated in microprocessor 64. This computed average value of body fat percentage and body weight are stored in memory 84 for further display as trend data.

To achieve more accurate averaged data, the previously stored values and the current values of body weight and body fat percentage may be weighted by a suitable weighting factor depending on the total number of measurements made during the one-week interval. The weighting factor ensures that measurements of the previously computed average value within one period are equally weighted to the current measured value within the same period, e.g. one week.

The following algorithm operated by software resident in microprocessor 64 may be used to calculate the new average value to be stored:

$$Y_{new} = \frac{i-1}{i} Y_{old} + \frac{1}{i} x$$

i—number of measurements
x—current measured value
$Y_{new}$—calculated value to be stored
$Y_{old}$—previously stored value In order to perform this computation, the number i of measurements made within the specified averaging period is also stored in memory 82.

The trending bar graphs 30, 32, which, as noted, respectively indicate the user's body weight and body fat percentage, may, as shown in FIG. 2, be subdivided into eight columns with 20 increments per column. Each of the columns represents a measurement trend interval, e.g. either an entire week or an entire month of averaged data, whereas each block in a column represents a fixed quantity of body weight or body fat percentage.

In an alternative procedure, body weight and body fat percentage trend data may be computed in 3- to 8-week intervals. That is, before week 3, no data is averaged and no trend is displayed; after week 8, the oldest data is removed from the trend display, e.g. week 1 is removed when week 9 is added; week 2 is removed when week 10 is added, and so on. The weekly average may be computed according to the following equation which is comparable to the previous equation:

$$\text{Weekly Avg.} = \frac{(\text{Current Week's Average} \times (n-1)) + \text{Data Just Measured}}{n}$$

Where n=number of measurements taken during the week including the most recent one.

The weekly averages as thus computed may then be mathematically "plotted" on a graph (i.e. these plots are used algorithmically and not shown on the display). The graph of average measurements would "appear" as points on a graph in which the week number (e.g. 3–8) is plotted on the x-axis and the average value of body data (weight and body fat percentage) is plotted on the y-axis. A least squares algorithm could then be used to determine the best fit of a line running through the "plotted" weekly averages. This algorithm would yield the Y=mX+b equation for such a line.

The slope m of this line indicates how much the weight or body fat percentage is changing per week, whereas the offset b indicates the weight or body fat percentage at week 0. Only the value and direction of the slope, which indicates how much the average is increasing or decreasing each week, need be calculated such as by the use of the following equation:

$$m = \frac{n\left(\sum_n (XY)\right) - \left(\sum_n X\right)\left(\sum_n Y\right)}{n\left(\sum_n X^2\right) - \left(\sum_n X\right)^2}$$

Where m=the slope of the line
n=the number of points in the graph
X=the week number
Y=the data value (either the weight or body fat)

As a further alternative, instead of displaying the absolute value of body fat percentage and body weight for each week and then plotting those values on a graph, three general trends may be indicated by three separate arrows on the LCD display.

In this trend display, an upward pointing arrow would indicate that the body weight or body fat percentage is increasing; a horizontal arrow would indicate that the data is stable; and a downward pointing arrow would indicate that the data is decreasing.

To aid a user in determining his/her progress, limits may be specified for the combination of increasing/decreasing trends, which may be skewed lower for the decreasing trend than for the increasing trend or which may be equal for both increasing and decreasing trends. In other words, the decreasing trend arrow would be presented or illuminated for a smaller weight loss than would the increasing trend arrow for a weight gain.

Body fat percentage trend is indicated, for example, as follows. If the slope m is smaller than, e.g., minus 0.5 percent per week (i.e. body fat percentage is decreasing more than 0.5 percent each week), the trend is decreasing and is shown on the LCD display as a downward sloping arrow. If the slope is greater than, e.g., 0.5 percent per week (body fat percentage is increasing more than 0.5 percent each week), the trend is increasing and is shown on the LCD display as an upward sloping arrow. All other slopes are considered to be stable data values and are shown with a horizontal arrow.

As a further option, weight trend can be indicated as follows. If the slope is smaller than, e.g. minus 0.7 Kg per week (i.e. weight is decreasing more than 0.7 Kg or equivalently 1.5 lbs each week), the trend is considered to be decreasing and is shown on the display as a downward sloping arrow. If the slope is greater than e.g., 0.7 Kg per week (weight is increasing more than 0.7 Kg or equivalently 1.5 lbs each week) the trend is considered to be increasing and is shown on the LCD display as an upward sloping arrow. All other slopes are considered to be stable data values and are shown with a horizontal arrow.

The microprocessor 64 may be programmed further to determine whether a body fat percentage or body weight measurement is performed at a recommended period of time of day or window (e.g. between 11:00 A.M. and 1:00 P.M.), and to store in memory 84 for a later trend display only those values of body weight and body fat percentage that were measured and computed during that interval.

A measurement of body fat percentage or body weight, for example, made at other times of the day will be displayed as current data, but will not be stored for future trend display. Alternatively, this value may be stored for future trend display if the value is corrected for the time of day of the measurement as described in the following section. This will ensure more reliable and repeatable body fat percentage and body weight trend data since the user's body fluid and electrolyte distribution and content, which may significantly affect the measurements of those factors, typically vary significantly during the day.

Figure 11:
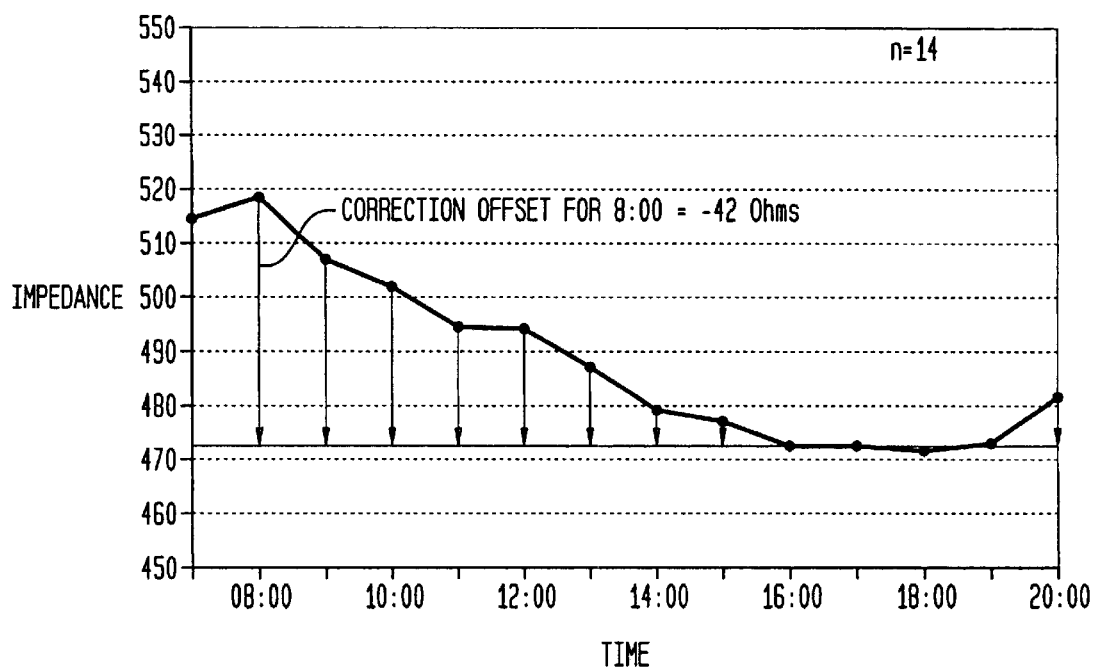
FIG. 11 is a graphical depiction of the correction of bioimpedance measurement as a function of the time the measurement was made in accordance with a possible implementation of the invention.

The algorithm used to compute body fat percentage from the measured bioimpedance may further include a correction factor that corrects for variations in the individual's measured weight, the time of day the measurement is made, and the ratio of intra and extracellular mass as measured by the computed bioimpedance. To this end, as shown in FIG. 11, the algorithm selects a reference time of day, say 4:00 p.m., and bioimpedance measurements taken at other times of day are modified, such as by adding or subtracting an offset or correction factor (impedance) from the current bioimpedance measurement. That correction factor, which could alternatively include a multiplying factor or any other function, depends on the time of day the measurement was taken, e.g., as shown in FIG. 11, 42 ohms at 8:00 a.m., 20 ohms at 11:00 a.m., etc.

In order to ensure privacy and security for the measured and stored body composition data, microprocessor 64 may further include a passive security algorithm, which compares, for example, the measured body weight and a computed body composition factor, such as body fat percentage, for a current user with the stored values of these body compositions factors that were obtained previously for authorized users of the system. If that comparison indicates that the measured body weight or computed body fat percentage of the current user differs from the previously measured values for the corresponding body composition factors stored in the system memory by more than a preset permissible deviation, say 5%, the current user is denied access to any of the stored body composition factors so that no stored or trend information will then be displayed. The permitted deviation between the current and stored values is preferably graduated so that a greater deviation is permitted between current and stored values taken, say, a month or two earlier, than would be permitted between a current and a prior measurement taken only a week or two earlier.

The passive security algorithm may be modified, as described below with reference to FIG. 9, to consider the personal identification codes of authorized users, which are stored in, and recognized by, the microprocessor 64. If a user enters an identification code number and obtains a measurement of his/her weight or body fat percentage, the algorithm compares these values with the stored values of those body composition factors for the user identified by the identification code entered by the current user. If the current data is within a specified deviation, say 5 percent, of the stored data, the microprocessor 64 automatically selects the correct personal data setting (e.g. height, sex, etc.) for that user and permits access to the user's stored or trend data. The permitted deviation between the current and the previous measurements may be graduated, as described above, to reflect increased periods between the dates of the current and prior body composition measurements. If, on the other hand, the current and stored values deviate by more than the predetermined, graduated amount, the current user is prevented from gaining access to the stored body composition data of the user whose ID code number was entered.

The above-described authorization checking procedure may be replaced, if desired, by a procedure that only checks the user's identification. To this end, microprocessor 64 may include a user-identification algorithm, which compares the user's current body weight and/or body fat percentage (impedance) measurements with previously stored values. Under this algorithm the microprocessor then automatically selects the correct personal data setting e.g. height, sex, etc., and/or former trend data or measurement date for that individual if the current and stored values deviate by not more than a predetermined amount. Thus, no additional identification, e.g. ID code or password is necessary. As an option, that information could also be requested, e.g. in case of doubt, i.e. if the deviation is too high or too close to the limit, or in case trend history data is to be used as well.

Figure 7:
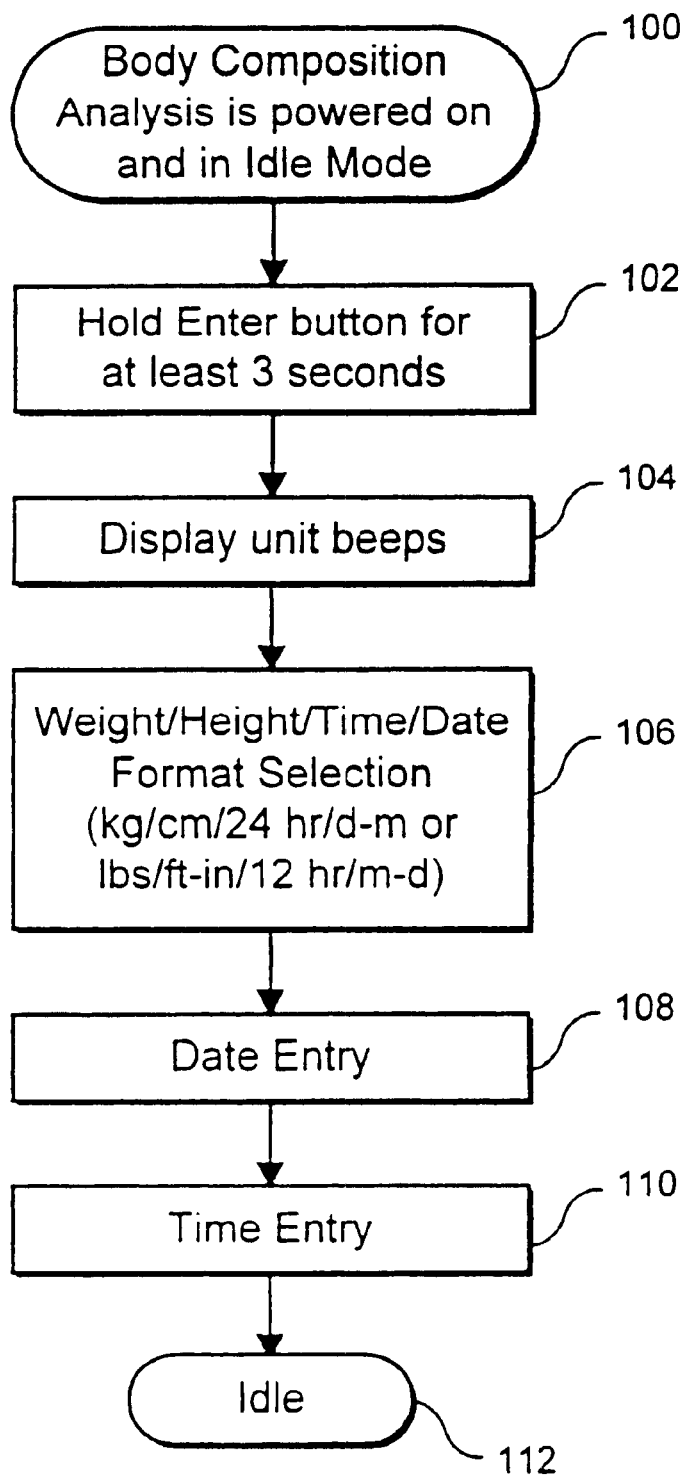

FIG. 7 illustrates the sequences that are taken at system startup in which a first-time user enters his/her setup parameters. The body composition analyzer is initially powered on and is in the idle mode at 100. The user then holds the enter button 38 on the base unit for at least 3 seconds as at 102. An indication such as an audible beep is then made in the display unit at 104 to request the user to enter the setup parameters.

At this time, through the operation of the up/down arrow buttons 40, the user at step 106 selects the desired format for displaying weight and height that is either in metric, i.e., kg, cm, day, month, 24-hour time, or in English units, i.e. lbs, ft/in, month/day, 12-hour time. The user again through the operation of the up down buttons 40 then enters the date at 108 and the time at 110. Once these steps are completed, the body composition analyzer returns to the idle mode of 112 and is now ready for use.

Figure 8:
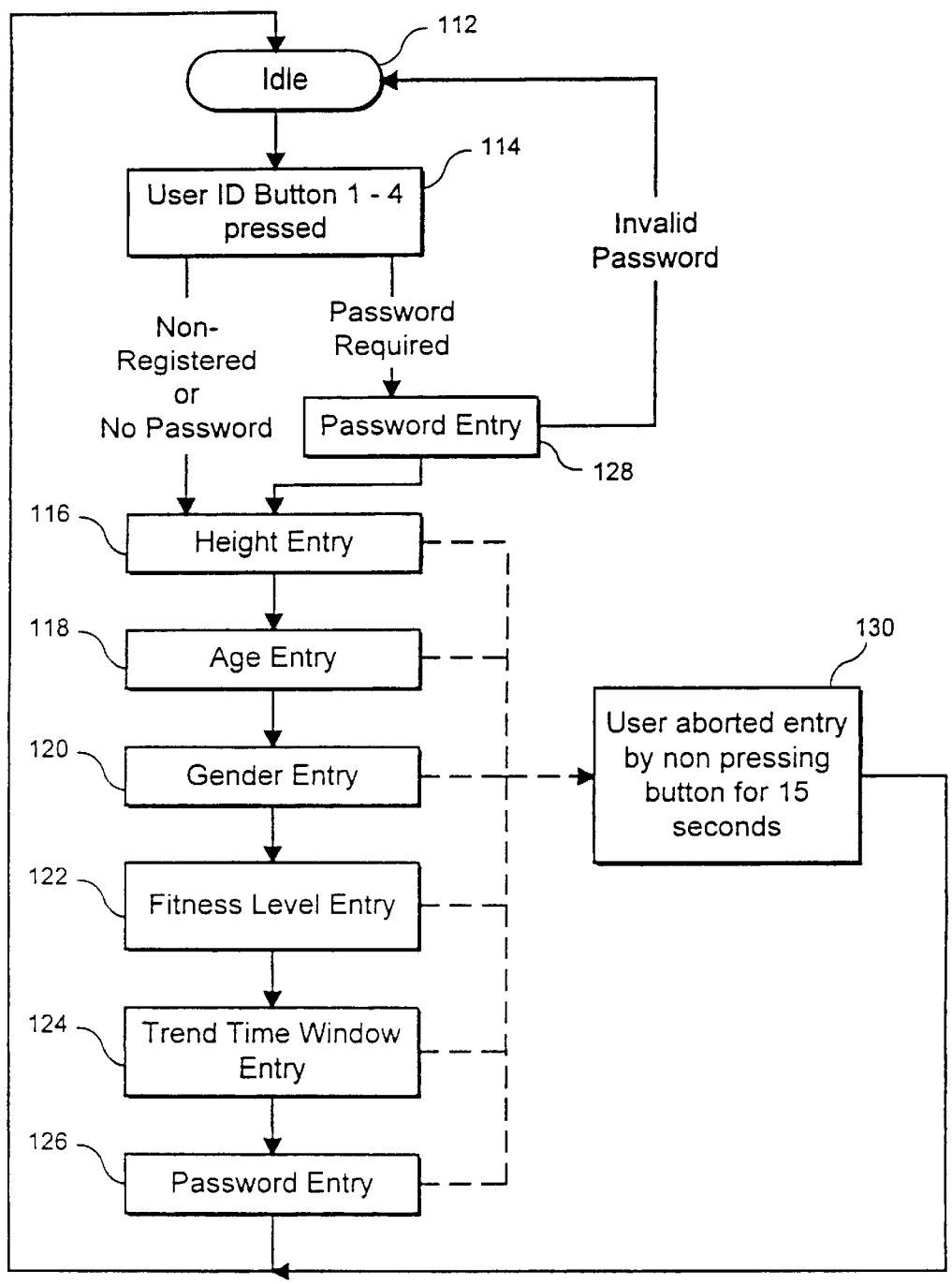

FIG. 8 illustrates the sequence of steps taken upon the completion of the setup sequence illustrated in FIG. 7 for a number of users (here four) to enter their personal identification data into the base unit microprocessor for use in subsequent body composition measurements. With the system in the idle mode at 112, the new user presses one of the personal ID number buttons 16 (1–4) that will thereafter be used each time the user makes a measurement. The unit then requests the user, by the use of the up/down buttons 40, to enter his/her height at 116, age at 118, gender at 120, and fitness level (e.g. a number from 1 to 5) at 122.

Upon the completion of these steps, the trend display window (typically two hours in duration) is set. As discussed previously, this time window represents the period during which an authorized user's measured body weight and body impedance values can be considered valid for use in computing the trend body composition averages. That is, data for measurements taken outside of this time window are not stored in memory 84 for use in computing the user's trend average. Stated differently, during regular use the user will be able to trend his/her measured weight and body fat percentage only if the body composition analyzer of the invention is used during the two-hour time window. The beginning and end of the time window is set at 124 by the operation of the up/down buttons 40.

After the completion of step 124, the user can then either waive or select a two-number password at 126. If the user elects to waive the use of a password, all subsequent measuring functions for that user that would otherwise require the use of a password, as described below with reference to FIG. 9 to carry out certain functions such as trending display measurements, will not require the user to insert a password. If the user wishes to select a password to achieve increased security, that is done by the use of the up/down buttons 40. Once this step is completed, the analyzer unit will return to its idle state at 112.

If desired, if one of the steps 116–126 is not completed by pressing the enter button 38 at a specified time, e.g. 15 seconds, after entering the relevant information, the unit, as indicated at 130, will assume that the user wishes to abort the operation, and the unit will return to the idle state without storing in its memory any of the previously entered information.

Figure 9:
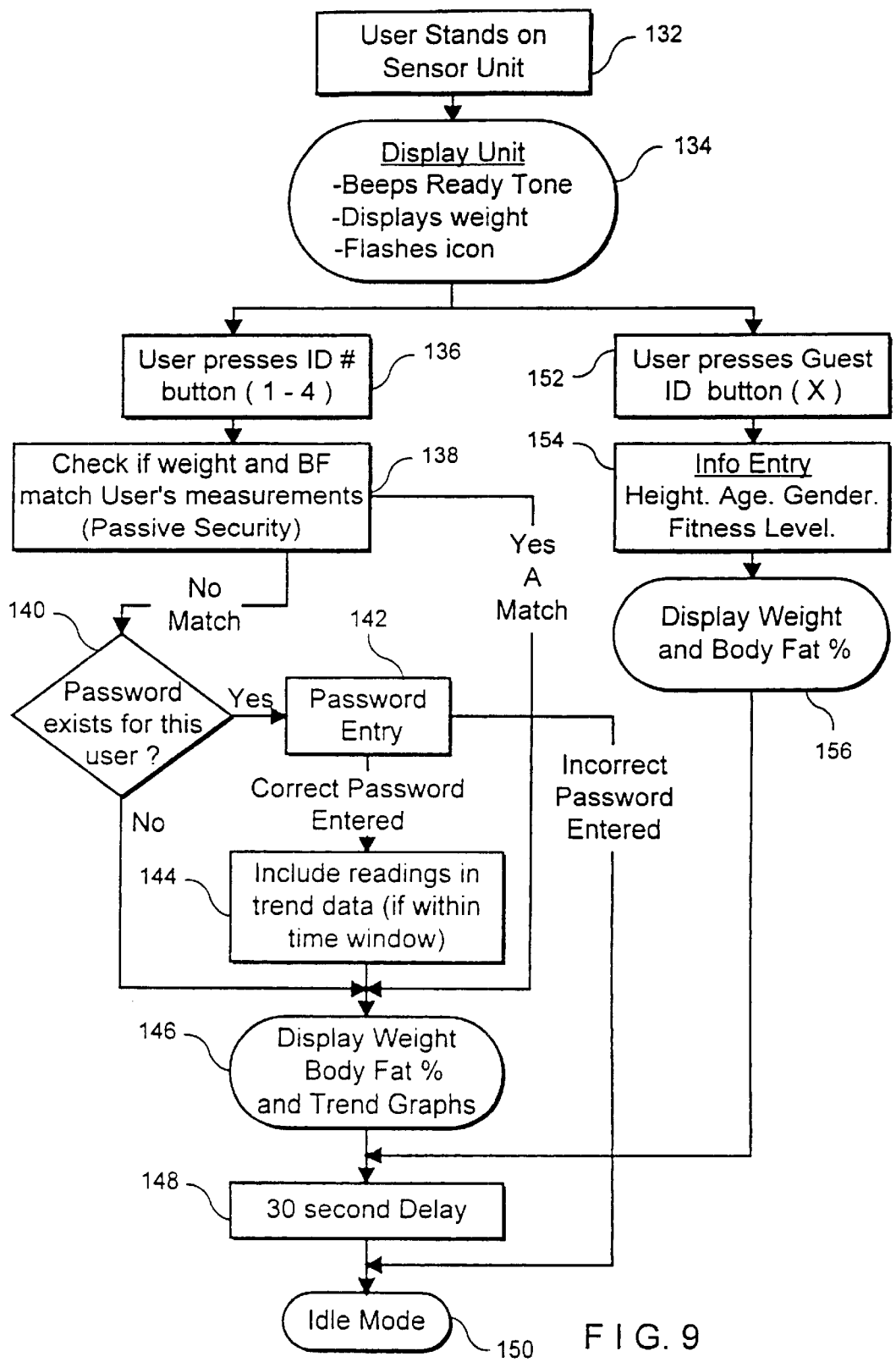

FIG. 9 illustrates the sequence of steps taken to measure and display current and trend body composition values both for an authorized user and a guest user. The user stands on the base sensor unit with his/her heels and toes in place for contact with the stimulus and sense electrodes as shown at 132. The display unit, as indicated at 134, then provides an audible ready beep and displays the user's weight. If the user has previously obtained an identification (ID) code number by carrying out the sequence of steps described in FIG. 7, he/she then presses the appropriate ID button 36, that is the button numbered 1, 2, 3 or 4 as at 136.

As a security and/or identification measure, the body composition analyzer program may include a passive security feature that permits the use of the system only by an authorized user. To this end, the user's current measured body weight and body fat percentage measurements are compared at 138 with the previous measurements of those parameters for the user identified by the ID number entered at step 136. If the user's current and previous weight and body fat percentage measurements do not match, that is, deviate by more than a significant amount, e.g. 5 percent, the unit then inquires at 140, if the user identified by the entered ID number had previously entered a password during the setup procedure described in FIG. 7. If the answer to this inquiry is "yes," the user is instructed at 142 to enter his/her previously established two-digit password. If the password entered matches the user's stored password, the analyzer system is instructed at 144 to include these current measurements to compute the user's trend data in the manner described above.

The LCD bar graph display 16, 18 displays at 146 the user's current measured weight and body fat percentage as well as the trend graphs for these body parameters. If the user had not previously selected a password, the operating sequence proceeds directly to the display step 146, which also occurs if a match between current and previous measurements is found at step 138. After a 30-second delay at 148 the display returns to its idle mode at 150. If, after step 142, the user has not entered the correct password, the display is cancelled and the system returns to its idle mode at 150.

Non-registered users, or guests, can only measure their body weight and body fat percentage. That is, since they have not previously entered any of their personal information (height, age, gender, fitness level, or password) into a pre-assigned ID number, a guest cannot obtain trend data for his/her weight and body fat percentage over time.

Measuring a guest's weight is accomplished in a manner similar to that of an authorized user. That is, a guest presses the guest ID button 35 at 152. If the guest wishes to view his/her current body fat percentage, he or she is required to enter his/her personal information (height, age, gender, fitness level) at 154.

Since the sensor unit has already measured the guest's bioimpedance, the entered personal information about the guest user allows the unit to calculate that user's percent body fat percentage, which information is displayed on the LCD graph display 18 as shown at 156. As in the case of an authorized user, after a 30-second delay at 148, the analyzer system returns to its idle mode at 150.

There may be times when a user wishes to view his/her previous measurements and the trend information that has been previously accumulated and stored in memory. To do this, he/she performs the steps illustrated in FIG. 10. As therein shown, the user presses the display trend button 34 at 158 and then presses the personal user ID button 36 that corresponds to the user's ID number at 160.

If the user has previously selected a password, the unit will prompt the user to enter that password at 164. If the correct password has been entered, a graph of the past trend information is displayed at 166 with the numerical values of the most recently measured average body weight and average body fat percentage being displayed at the top of the LCD display. The up-down arrow buttons 40 are then scrolled through the data for the previous weeks or months, which will cause the bar for the currently displayed week or month to become solid and the next week/month bar in the succession to begin flashing in a "top-down fill" fashion. The corresponding values for the bar will be displayed in the upper half of the LCD display at 170.

For example, if the data shown on the LCD display includes a graphical trend of eight months of data, pressing the down arrow button 40 will cause the weight and body fat percentage graph columns for month 8 to stop flashing. The weight and body fat graph columns will then begin flashing in a "top down fill" mode, and the numerical values for the weight and body fat percentage numerical values for month 8 will be replaced with the average weight and body fat percentage values for month 7.

If the user continues to press the down arrow button, the weight and body fat percentage values for month 7 will be replaced with that for month 6's body weight and body fat percentage values, and month 7's columns will stop flashing while month 6's column will begin flashing in the "top down fill" mode. The up arrow button accomplishes the same function as the down arrow button, but in the opposite chronological direction (i.e. the data/graphs for month 1 would be shown first, followed by those for month 2, etc.).

Once the user has completed his/her operation of the up/down buttons 40, after a 30-second delay at 172 the display returns to the idle mode at 174 in which only the time and date are displayed. If an incorrect password is entered at step 164, the user's current and trend data will not be displayed and the display is placed directly into the idle mode.

In addition to displaying the user's body weight and percent body fat percentage, the body composition analyzer of the invention may, as noted above, also allows the user to view other body composition factors such as lean body mass, his/her fat free mass (FFM), body mass index (BMI), total body water, and blood pressure. These values and their corresponding trend graphs may be displayed on the LCD display in the same location as (i.e. they replace) the body fat percentage values and trend chart, by toggling the button 24 through these three values.

That is, when the system is first used, body fat percentage is displayed. If the user selects one of the other data formats (fat free mass or body mass index) that new format will remain in effect until it is changed by the operation of the %BF, FFM, BMI button 24. For example, if a user takes his/her measurements and presses button 24 (the LCD then displays weight and fat free mass), the next time he/she takes a measurement or displays trend data, the LCD display will automatically display both weight and fat free mass.

It will be understood that the body composition analyzer of the present invention, as described hereinabove, provides accurate current and trend data of at least two selected body composition factors, such as body fat percentage and body weight. It will be further understood that modifications may be made to the described embodiments of the invention without necessarily departing from the spirit and scope of the invention.

What is claimed is:

1. A system for measuring and displaying body composition information comprising means for measuring a current value of at least one body composition factor, means for storing the results of measurements of said at least one body composition factor taken over a plurality of prior intervals, means for computing and storing an average value of said at least one body composition factor measured during one or more of said prior intervals in an event more than one such measurement of said at least one body composition factor is made during said one or more prior intervals, and means operatively coupled to said storing means for displaying the results of the current measurement along with data representative of at least one prior measurement of said at least one body composition factor.

2. The system of claim 1, in which said displaying means comprises a graphic display of the results of the current and at least one prior measurement of at least two body composition factors.

3. The system of claim 2, in which said body composition factors include body weight and body fat percentage.

4. The system of claim 3, further comprising means for measuring the user's body weight and bioimpedance, and means for computing the user's body fat percentage from said measured weight and bioimpedance.

5. The system of claim 1, further comprising means for inputting one of a plurality of user identification codes, each of said codes being associated with one of a corresponding plurality of potential users, said displaying means being operative to display body composition data only for the user identified by the inputted personal identification code.

6. A system for measuring and displaying body composition information comprising means for measuring a current value of at least one body composition factor, means for storing the results of measurements of said at least one body composition factor taken over a plurality of prior intervals means for computing and storing an average value of said at least one body composition factor measured during one or more of said prior intervals in an event more than one such measurement of said at least one body composition factor is made during said one or more prior intervals, means operatively coupled to said storing means for displaying the results of the current measurement along with data representative of at least one prior measurement of said at least one body composition factor, means for comparing a current body composition measurement against a stored value of body composition measurement against a stored value of body composition measurement, and means for preventing access to the stored body composition data if the stored body composition deviates front the current body composition data by a predetermined amount.

7. A system for measuring and displaying body composition information comprising means for measuring a current value of at least one body composition factor, means for storing the results of measurements of said at least one body composition factor taken over a plurality of prior intervals, means for computing and storing an average value of said at least one body composition factor measured during one or more of said prior intervals in an event more than one such measurement of said at least one body composition factor is made during said one or more prior intervals, means operatively coupled to said storing means for displaying the results of the current measurement along with data representative of at least one prior measurement of said at least one body composition factor, and means for storing body composition measurement data only for measurements of a body composition factor taken during a predetermined period time of day.

8. The system of claim 1, further comprising means for storing body measurement data only for measurements of a body composition factor taken during a predetermined period of time of day.

9. The system of claim 1, comprising a base unit including said measuring means and a display unit remote from said base unit, said remote display unit including said displaying means, and means in said base unit for transmitting current and prior body composition data from said base unit to said remote display unit.

10. The system of claim 1, in which said body composition factor includes one or more of body weight, body fat percentage, fat free mass, lean body mass, body mass index, and total water content.

11. The system of claim 10, in which said displaying means comprises a graphic display of the results of the current and at least one prior measurement of at least two body composition factors.

12. The system of claim 11, in which said body composition factors include body weight and body fat percentage.

13. The system of claim 12, further comprising means for measuring the user's body weight and means for computing the user's bioimpedance, and means for computing at least one other body composition factor from said value of bioimpedance.

14. The system of claim 4, comprising a base unit including said measuring means and a display unit remote from said base unit and including said displaying means, and means in said base unit for transmitting the current and prior body composition data from said base unit to said remote display unit.

15. The system of claim 14, in which said transmitting means includes an infrared transmitter, said display unit comprising an infrared receiver.

16. A body composition display system comprising means for measuring and computing at least first and second different body composition factors of a user, means coupled to said measuring and computing means for storing data representative of at least one measurement of said first and second body composition factors made during at least one prior time interval, and means coupled to said storing means for displaying said at least one prior measured value of said first and second body composition factors, along with a display of the current values of said first and second body composition factors.

17. The system of claim 16, in which said body composition factors include body weight and body fat percentage, said measuring means comprising means for measuring the user's bioimpedance and means for deriving therefrom a signal representative of the user's body weight.

18. The system of claim 16, further comprising means for inputting one of a plurality of personal identification codes, said displaying means being effective to display body composition data only for the user identified by the inputted personal identification code.

19. The system of claim 16, further comprising means for computing the average values of body weight and body fat percentage taken during one or more of said prior intervals in the event more than one of such measurements is made during that prior interval.

20. The system of claim 16, further comprising means for inputting one of a plurality of personal identification codes, each of said codes being associated with one of a corresponding plurality of users, said displaying means, in response to said input code, displaying body composition data only for the user identified by the inputted personal identification code.

21. The system of claim 20, further comprising means for computing the average values of body weight and body fat percentage taken during one of said prior intervals in the event more than one of such measurements is made during that interval.

22. The system of claim 21, in which said means for computing body fat percentage includes means for measuring the user's bioimpedance, said bioimpedance measuring means including a current source, a first pair of electrodes coupled to said current source, a second pair of electrodes, and means for measuring the voltage drop across said second pair of electrodes.

23. The system of claim 16, in which said measuring means and said computing means are included in a base sensor unit, and said displaying means is included in a display unit remote from said base sensor unit, said base sensor unit comprising means coupled to said computing means for transmitting the computed body composition data to said remote display unit.

24. The system of claim 23, in which said transmitting means includes an infrared transmitter, said display unit comprising an infrared receiver.

25. The system of claim 22, in which said measuring means and said computing means are included in a base sensor unit, and said displaying means is included in a display unit remote from said base sensor unit, said base sensor unit comprising means coupled to said computing means for transmitting the computed body composition data to said remote display unit.

26. The system of claim 25, in which said transmitting means includes an infrared transmitter, said display unit comprising an infrared receiver.

27. A system for measuring and displaying current and previously measured body composition factors for a plurality of authorized users, said system comprising security or identification means for comparing a current body factor measurements and prior stored body composition measurements, and means effective to preclude the current user from gaining access to stored body composition data if the current and stored body composition data deviate by more than a predetermined amount.

28. The system of claim 27, in which a displaying means comprises a graphic display of the results of the current and at lest one prior measurement of at least two body composition factors.

29. The system of claim 28, in which a measuring means and said computing means are included in a base sensor unit, and said displaying means is included in a display unit remote from said base sensor unit, said base sensor unit comprising means coupled to said computing means for transmitting the computed body composition data to said remote display unit.

30. The system of claim 27, in which said security means includes means for comparing the current body composition measurements with prior body composition measurements for a user identified by the identification code entered by the current user.

31. The system of claim 27, further comprising means for storing body measurement data only for measurements taken during a predetermined period of time of day.

32. A system for measuring and displaying body composition factors for a plurality of potential users including means for displaying the results of current and prior body composition measurements, means for inputting one of a plurality of user identification codes, each of said codes being associated with one of a corresponding plurality of potential users, and means for permitting a display of stored body composition information only for the user identified by the inputted user identification code.

33. The system of claim 32, further comprising means for storing body measurement data only for measurements taken during a predetermined period of time of day.

34. The system of claim 32, further comprising means for comparing a current body composition measurement against the stored value of an authorized user's body composition measurement, and means for preventing access to the stored measurement data if the stored measurement data deviates from the current measurement data by a predetermined amount.

35. The system of claim 33, further comprising means for comparing a current body composition measurement against the stored value of an authorized user's body composition measurement, and means for preventing access to the stored measurement data if the stored measurement data deviates from the current measurement data by a predetermined amount.

36. A system for measuring and displaying measured body composition factors comprising means for measuring body composition factors, means for storing the results of current and prior body composition measurements, and means for storing in said storing means only the results of a body composition measurement taken during a predetermined time of day.

37. The system of claim 36, in which said body composition factor includes one or more of body weight, body fat percentage, fat free mass, lean body mass, body mass index, and total water content.

38. The system of claim 36, further comprising means for comparing a current body composition measurement against the stored value of an authorized user's body composition measurement, and means for preventing access to the stored measurement data if the stored measurement data deviates from the current measurement data by a predetermined amount.

39. The system of claim 36, in which said displaying means comprises a graphic display of the results of the current and at lest one prior measurement of at least two body composition factors.

40. The system of claim 36, in which said body composition factors include body weight and body fat percentage.

41. The system of claim 36, in which said measuring means and said computing means are included in a base sensor unit, and said displaying means is included in a display unit remote from said base sensor unit, said base sensor unit comprising means coupled to said computing means for transmitting the computed body composition data to said remote display unit.

42. The system of claim 41, in which said transmitting means includes an infrared transmitter, said display unit comprising an infrared receiver.

43. A system suitable for home use for measuring and displaying at least one body composition factor comprising a base unit and a display unit remote from said base unit, said base unit including means for measuring said at least one body composition factor and means for storing the result of the measurement of said body composition factor, said remote display unit including means for displaying the results of a current and at least one prior measurement of said body composition factor, and means in said base unit for transmitting stored and current body composition information to said remote display unit.

44. The system of claim 43, in which said body composition factor includes one or more of body weight, body fat percentage, fat free mass, lean body mass, body mass index, and total water content.

45. The system of claim 43, in which said body composition factors include body weight and body fat percentage.

46. The system of claim 44, in which said means for computing body fat percentage includes means for measuring the user's bioimpedance, said bioimpedance measuring including a current source, a first pair of electrodes coupled to said current source, a second pair of electrodes, and means for measuring the voltage drop across said second pair of electrodes.

47. The system of claim 43, in which said displaying means comprises a graphic display of the results of the current and at least one prior measurement of at least two body composition factors.

48. The system of claim 47, in which said body composition factors include body weight and body fat percentage.

49. The system of claim 43, further comprising means for inputting one of a plurality of user identification codes, each of said codes being associated with one of a corresponding plurality of potential users, said display means displaying body composition data only for the user identified by the inputted personal identification code.

50. The system of claim 43, further comprising means for comparing a current body composition measurement against the stored value of an authorized user's body composition measurement, and means for preventing access to the stored measurement data if the stored measurement data deviates from the current measurement data by a predetermined amount.

51. The system of claim 50, further comprising means for storing body measurement data only for measurements taken during a predetermined period of time of day.

52. The system of claim 43, in which said transmitting means includes an infrared transmitter, said display unit comprising an infrared receiver.

53. A system for measuring and displaying at least one body composition factor of an individual comprising means for measuring the individual's bioimpedance, and means for modifying the measured bioimpedance by an amount based on the time of day the measurement is made.

54. The system of claim 53, in which said body composition factor is body fat percentage.

55. The system of claim 53, in which said measuring means is included in a base sensor unit, and further including means for displaying the measured body composition factor, said display means being included in a display unit remote from said base sensor unit.

56. The system of claim 55, in which said base sensor unit includes means operatively coupled to said measuring means for transmitting data representative of the measured body composition factor to said display unit.

57. A system for measuring and displaying body composition information comprising means for measuring the current value of a body composition factor which includes at least the user's body fat percentage, means for storing the results of a measurement of said body composition factor taken during said at least one prior interval, and means operatively coupled to said storing means for displaying the results of the current measurement of the user's body fat percentage along with data representative of said at least one prior measurement of the user's body fat percentage.

58. The system of claim 57, in which said displaying means comprises a graphic display of the results of the current and said at least one prior measurement of the user's body fat percentage and of at least one additional body composition factor.

59. The system of claim 58, in which said additional body composition factor includes body weight.

60. The system of claim 57, further comprising means for measuring the user's body weight and bioimpedance, and means for computing the user's body fat percentage from said measured weight and bioimpedance.

61. The system of claim 57, further comprising means for inputting one of a plurality of user identification codes, each of said codes being associated with one of a corresponding plurality of potential users, said displaying means being operative to display body composition data only for the user identified by the inputted personal identification code.

62. The system of claim 57, further comprising means for comparing a current body composition measurement against a stored value of body composition measurement, and means for preventing access to the stored body composition data if the stored body composition data deviates from the current body composition data by a predetermined amount.

63. The system of claim 57, comprising a base unit including said measuring means and a display unit remote from said base unit, said remote display unit including said displaying means, and means in said base unit for transmitting current and prior body composition data from said base unit to said remote display unit.

* * * * *